(12) United States Patent
Zhang et al.

(10) Patent No.: US 12,193,458 B2
(45) Date of Patent: Jan. 14, 2025

(54) SWEETENING COMPOSITION AND PREPARATION METHOD AND USE THEREOF

(71) Applicant: HUNAN NUTRAMAX INC., Hunan (CN)

(72) Inventors: Baotang Zhang, Hunan (CN); Jiazhong Tan, Hunan (CN)

(73) Assignee: HUNAN NUTRAMAX INC., Hunan (CN)

( * ) Notice: Subject to any disclaimer, the term of this patent is extended or adjusted under 35 U.S.C. 154(b) by 304 days.

(21) Appl. No.: 16/966,861

(22) PCT Filed: May 31, 2019

(86) PCT No.: PCT/CN2019/089408
§ 371 (c)(1),
(2) Date: Jul. 31, 2020

(87) PCT Pub. No.: WO2020/155494
PCT Pub. Date: Aug. 6, 2020

(65) Prior Publication Data
US 2021/0352943 A1 Nov. 18, 2021

(30) Foreign Application Priority Data
Jan. 30, 2019 (CN) .......................... 201910089267.5

(51) Int. Cl.
*A23L 27/10* (2016.01)
*A23L 2/60* (2006.01)
(Continued)

(52) U.S. Cl.
CPC .................. *A23L 27/11* (2016.08); *A23L 2/60* (2013.01); *A23L 3/365* (2013.01); *A23L 3/405* (2013.01);
(Continued)

(58) Field of Classification Search
CPC . A23L 27/11; A23L 2/60; A23L 3/365; A23L 3/405; A23L 5/273; A23L 27/36;
(Continued)

(56) References Cited

U.S. PATENT DOCUMENTS

2013/0040033 A1 2/2013 Markosyan
2015/0118379 A1 4/2015 Markosyan

FOREIGN PATENT DOCUMENTS

CN 101003552 A 7/2007
CN 100404523 C * 7/2008
(Continued)

OTHER PUBLICATIONS

CN-101941997-A (Clarivate machine Translation) (Year: 2011).*
(Continued)

*Primary Examiner* — Donald R Spamer
*Assistant Examiner* — Andrew E Merriam
(74) *Attorney, Agent, or Firm* — Knobbe, Martens, Olson & Bear, LLP (57) ABSTRACT

This application relates to a sweetening composition and a preparation method and use thereof. The method includes steps of obtaining mesophyll fragments of *Rubus suavissimus* S. Lee, extracting with water as a solvent, removing phenolic hydroxyl-containing components, concentrating, purifying, and water-phase crystallization to obtain a sweetening composition. The sweetening composition is white in color, with unobvious bitterness astringent taste. The sweetening composition contains 50% to 99% of Rubusoside based on a dry weight, and has an absorbance of less than 0.4 at a wavelength of 270 to 370 nm after being dissolved and prepared into an aqueous solution (with a solid content of 1%, w/w). By removing bitter glycosides and phenolic hydroxyl-containing components, this application makes the flavor of the sweetening composition better. In the prepara- (Continued)

tion process of the sweetening composition of the this application, only purified water is used and no organic solvents are used.

18 Claims, 2 Drawing Sheets

(51) Int. Cl.
| | |
|---|---|
| *A23L 3/365* | (2006.01) |
| *A23L 3/40* | (2006.01) |
| *A23L 5/20* | (2016.01) |
| *A23L 27/30* | (2016.01) |
| *A23L 33/105* | (2016.01) |
| *B01D 61/02* | (2006.01) |
| *B01D 61/04* | (2006.01) |
| *B01D 69/02* | (2006.01) |

(52) U.S. Cl.
CPC .............. *A23L 5/273* (2016.08); *A23L 27/36* (2016.08); *A23L 33/105* (2016.08); *B01D 61/027* (2013.01); *B01D 61/04* (2013.01); *B01D 69/02* (2013.01); *A23V 2002/00* (2013.01); *B01D 2311/02* (2013.01); *B01D 2311/18* (2013.01); *B01D 2311/2619* (2013.01); *B01D 2311/2626* (2013.01); *B01D 2311/2642* (2013.01); *B01D 2311/2649* (2013.01); *B01D 2311/2676* (2013.01); *B01D 2325/0283* (2022.08)

(58) Field of Classification Search
CPC .............. B01D 61/027; B01D 2311/02; B01D 2311/2619; B01D 2311/2626; B01D 2311/2649; B01D 2311/2676; B01D 2325/02

See application file for complete search history.

(56) References Cited

FOREIGN PATENT DOCUMENTS

| | | | | | |
|---|---|---|---|---|---|
| CN | 101669643 | A | * | 3/2010 | |
| CN | 101941997 | A | * | 1/2011 | |
| CN | 102239983 | A | | 11/2011 | |
| CN | 102702284 | A | | 10/2012 | |
| CN | 102838644 | A | | 12/2012 | |
| CN | 104193788 | A | | 12/2014 | |
| CN | 104262425 | A | | 1/2015 | |
| CN | 105061526 | A | | 11/2015 | |
| CN | 105153252 | A | | 12/2015 | |
| CN | 105381628 | A | * | 3/2016 | |
| CN | 106236808 | A | * | 12/2016 | ............. A61K 36/28 |
| CN | 108276462 | A | | 7/2018 | |
| CN | 108516997 | A | | 9/2018 | |
| CN | 109717445 | A | | 5/2019 | |
| JP | 2018108033 | A | * | 7/2018 | |

OTHER PUBLICATIONS

CN-105381628-A (Clarivate machine Translation) (Year: 2016).*
CN-106236808-A (Clarivate machine Translation) (Year: 2016).*
CN-108516997-A (Clarivate machine Translation) (Year: 2018).*
CN-100404523-C (Espace.net translation) (Year: 2008).*
CN-101669643-A (Clarivate machine translation) (Year: 2010).*
JP-2018108033-A (Clarivate machine translation) (Year: 2018).*

* cited by examiner

SWEETENING COMPOSITION AND PREPARATION METHOD AND USE THEREOF

CROSS REFERENCE

The present application claims priority from Chinese patent application No. 201910089267.5, entitled "Sweetening composition and preparation method and use thereof" filed on Jan. 30, 2019, the entire disclosure of which is incorporated herein by reference in its entirety.

TECHNICAL FIELD

The present invention relates to the field of extraction technology, in particular to a sweetening composition and preparation method and use thereof.

BACKGROUND ART

*Rubus suavissimus* S. Lee of Rosaceae, also known as *Rubus chingii* var. *suavissimus* (S. K. Lee) L. T. Lu, is mainly produced in Guangxi province and also named as Guangxi sweet tea. It was named *Rubus suavissimus* S. Lee by the botanist Li Shugang in 1981 and described in detail. The sweet taste component in *Rubus suavissimus* S. Lee is a diterpene glycoside component, wherein the content of Rubusoside is the highest. Besides the Rubusoside, *Rubus suavissimus* S. Lee also contains Steviolmonoside, Suavioside A, and Suaviosides B, G, H, I and J and the like, which have sweet taste; Suaviosides D1 and E, Paniculoside IV and the like, which are tasteless; and Sugereoside, Nigaichigoside F1, Suaviosides C1, D2 and F and the like, which have bitter taste. The sweetness of Rubusoside is about 200 times of sucrose, and the sweet taste thereof is cool and refreshing at low concentrations. Rubusoside has a faint fragrance when being heated and can be used in essences and flavors. Rubusoside has good thermal stability, is not easy to be oxidatively decomposed, and will not decompose significantly when being heated in a water solution at a pH value of 3 to 12 at a temperature under light irradiation. The special flavor and properties of Rubusoside enable it to be used more and more widely in the fields of foods, beverages, health products and the like.

The patent application with publication No. CN101003552A introduces a process comprising extracting with water or an ethanol water solution, resin adsorbing, eluting with ethanol, removing impurities with polyamide resin or ion exchange resin or alumina, concentrating, drying, then dissolving with anhydrous alcohol and crystallizing to obtain high-purity Rubusoside.

The patent application with publication No. CN102239983A provides a method comprising extracting with a water-ethanol solution, filtering, concentrating, resin adsorbing, desorbing with ethanol, decolorizing with activated carbon after concentration, and crystallizing and recrystallizing with an ethanol solution to obtain a pure product of Rubusoside.

In the production process described in the patent application with publication No. CN102702284A, Rubusoside with a content ≥98% is obtained by extraction, concentration, flocculation, clarification, centrifugation, macroporous resin adsorption, desorption with alcohol solution, decolorization with ion exchange resin, desalting, decolorization again, then concentration and drying.

In the method provided by the patent application with publication No. CN104262425A, a finished product is obtained by pulverizing raw materials, solvent extracting, membrane concentrating, centrifuging, adjusting the pH of the feed liquid until the liquid is acidic, loading on a macroporous adsorption resin, treating with alkaline and acid, eluting with an ethanol solution, concentrating, treating with a composite ion exchange resin, concentrating, crystallizing with organic reagents such as methanol and acetone, dissolving the crystals with water and drying.

The extraction method provided by the patent application with publication No. CN104193788A comprises the steps of adding a surfactant or a composite enzyme to perform microwave extraction on raw materials, then concentrating into a paste, precipitating with an ethanol water solution, centrifuging, purifying with a macroporous adsorption resin, desorbing with ethanol, decolorizing with an ion exchange resin, and purifying with a polyamide resin to obtain a white finished product.

The method described in the patent application with publication No. CN108276462A comprises pulverizing raw materials, carrying out flash extraction, centrifuging via two different centrifugal means, adjusting the pH of the feed liquid until the liquid is acidic, loading on a macroporous adsorption resin, treating with alkaline and acid, desorbing with an ethanol solution, enzymolyzing, decolorizing by stages with an organic membrane, concentrating, crystallizing with a methanol or ethanol solvent, and drying to obtain a finished product.

In the method provided by the patent application with publication No. CN105061526A, Rubusoside with a content ≥99% is obtained by pulverizing raw materials, sieving, carrying out microwave countercurrent extraction, centrifuging, adjusting the pH value of the feed liquid until the liquid is alkaline, loading on a macroporous adsorption resin, then desorbing with hydrophilic solvents such as ethanol, ultrafiltering, concentrating, crystallizing and recrystallizing with methanol or ethanol.

The US patent US20150118379A1 provides a method for the preparation of Rubusoside, comprising the following steps: subjecting high-purity stevioside to enzymolysis with a mixed enzyme added to generate a Rubusoside mixture, then inactivating the enzyme at high temperature, followed by adsorbing with a macroporous adsorption resin, desorbing with an alcohol solution, concentrating and drying to obtain a finished product. In addition, the method may also comprise the following steps: drying the mixture after inactivating the enzyme, then dissolving and crystallizing with an alcohol solution, and recrystallizing twice with an alcohol solution to obtain a finished product.

The purification of Rubusoside in the above patents mostly requires the use of a macroporous adsorption resin for adsorption, then the impurities are eluted with water or an acid solution and an alkali solution, and Rubusoside is desorbed from the resin with an alcohol solution, and moreover, organic reagents are required for crystallization and recrystallization. During the whole process, the purification with a macroporous adsorption resin uses a large amount of water for washing to elute impurities, especially when the impurities are eluted with an acid-alkali solution, a large amount of water is required for washing the resin to neutral, resulting in a large amount of wastewater generated, and the wastewater treatment cost is relatively high. The use of an alcohol solutions and an organic solvent for desorption and crystallization in the process will create obstacles and difficulties in the production of organic products. In addition, the cost of organic alcohol used in production is very high, and residual solvents in the product will affect the quality of the product.

SUMMARY OF THE INVENTION

The technical problem to be solved by the present invention is that, a large amount of organic reagents are required to extract a sweetening composition from leaves of *Rubus suavissimus* S. Lee in the prior art, which has the disadvantages of high cost, environmental unfriendliness, and the residual organic solvents affecting the quality of the product.

In order to solve the above technical problem, the present invention provides a sweetening composition and preparation method and use thereof.

A method for preparing a sweetening composition from leaves of *Rubus suavissimus* S. Lee, comprising the following steps:
  S1. pretreatment: crushing the raw materials, removing the leaf tissues rich in bitter glycosides, and obtaining mesophyll fragments;
  S2. extraction: extracting the mesophyll fragments with water as a solvent to obtain an extract solution;
  S3. removal of phenolic hydroxyl-containing components: allowing the extract solution to pass through a polar macroporous adsorption resin such that the phenolic hydroxyl-containing components are adsorbed, and collecting the effluent;
  S4. concentration and purification with a nanofiltration membrane: allowing the effluent collected in step S3 to pass through a nanofiltration membrane with a pore diameter of 1 to 2 nm for concentrating and purifying, and retaining a retentate solution; and
  S5. water phase crystallization: freezing the retentate solution obtained in step S4 into a solid, then thawing, and crystallizing at a temperature of 0° C. to 10° C. to obtain crystals of a sweetening composition.

Preferably, in step S1, a cyclonic separation method is used to remove the leaf tissues rich in bitter glycosides, and to separate and collect the mesophyll fragments.

Preferably, in step S2, the extraction of the crushed leaves of *Rubus suavissimus* S. Lee is performed with water as a solvent using a continuous countercurrent extractor to obtain an extract mixture, and then the extract mixture is squeezed with a squeezer, followed by filtering to obtain the extract solution.

Preferably, the extraction time for obtaining the extract mixture by extracting using a continuous countercurrent extractor is 30 to 120 min, the extraction temperature is 40 to 90° C., and the material-to-liquid ratio of the crushed leaves of *Rubus suavissimus* S. Lee to the water is 1 kg: (3 to 6) L.

Preferably, in step S2, the extraction of the crushed leaves of *Rubus suavissimus* S. Lee is performed with water as a solvent using a high-pressure jet extractor, followed by centrifuging and filtering to obtain the extract solution.

Preferably, the time for performing the extraction using a high-pressure jet extractor is 15 to 180 min, the fluid temperature is 5 to 100° C., the fluid pressure is 3 to 100 MPa, and the material-to-liquid ratio of the crushed leaves of *Rubus suavissimus* S. Lee to the water is 1 kg: (3 to 5) L.

Preferably, in step S3, the polar macroporous adsorption resin is selected from a phenolic resin, or a styrene-divinyl-benzene resin with a skeleton structure containing one or more of amide, sulfoxide, cyano, amino, pyridine, and nitrogen oxide groups, or a polyacrylic resin with a skeleton structure containing one or more of amide, sulfoxide, cyano, amino, pyridine, and nitrogen oxide groups.

Preferably, prior to step S3, the following steps are also comprised: adding a precipitating agent to the extract solution and stirring, filtering, collecting the filtrate, adjusting the pH value of the filtrate to 3 to 6, and then treating the filtrate having pH adjusted to remove phenolic hydroxyl-containing components Preferably, the precipitating agent is added to the extract solution at a temperature of 50 to 60° C., and the precipitating agent is preferably one or more of quicklime, slaked lime and calcium bicarbonate.

Preferably, in step S5, the retentate solution is subjected to the freezing, thawing and crystallizing, under ultraviolet light irradiation.

The present invention also includes a sweetening composition prepared by the above method for preparing a sweetening composition from leaves of *Rubus suavissimus* S. Lee.

In addition, the present invention also provides the use of the sweetening composition in foods, beverages, health products, daily chemicals and medicines.

The beneficial effects of the present invention compared with the prior art include:

the raw materials are crushed and the leaf tissues rich in bitter glycosides are removed to obtain mesophyll fragments, thereby effectively removing bitter glycosides that are difficult to be separated in subsequent processes; water is used as a solvent for extraction to obtain an extract solution which contains no organic solvents and is harmless to human health; the phenolic hydroxyl-containing components are adsorbed by a polar macroporous adsorption resin because the components having strong polarity will be adsorbed by the polar macroporous adsorption resin, and it is difficult for solvent water to desorb these components; the monosaccharides, disaccharides, and partial amino acids in the extract solution are not easy to be adsorbed, and flow out directly with the solution; Suavioside and the rest diterpene glycoside components such as Steviolmonoside, Suavioside A and Suaviosides B, G, H, I and J and the like are not only adsorbed, but also desorbed by a water solution; compared with diterpene glycoside components, phenolic hydroxyl-containing polyphenols and flavonoids are more easily adsorbed by the polar macroporous resin;

an alcohol solution with a high content is required in order to desorb these phenolic hydroxyl-containing components; therefore, the phenolic hydroxyl-containing components can be removed; then concentrating and purifying are carried out using a nanofiltration membrane with a pore size of 1 to 2 nm, and the retentate solution is retained; concentrating and purifying by nanofiltration can remove most of the water, inorganic salts, amino acids, monosaccharides, disaccharides, organic acids and the like; afterwards, the retentate solution is frozen into a solid, then thawed and crystallized at a temperature of 0° C. to 10° C. to obtain crystals of a sweetening composition; thus, a sweetening composition can be obtained by preparing an extract solution without using organic solvents, in combination with the step of removing the phenolic hydroxyl-containing components in the extract, followed by concentrating, purifying and crystallizing, and the obtained sweetening composition has a pure taste and white color, with almost no bitter taste.

BRIEF DESCRIPTION OF THE DRAWINGS

The features and advantages of the present invention will be more clearly understood by referring to the drawings, which are schematic and should not be construed as limiting the present invention in any way.

DETAILED DESCRIPTION OF THE PREFERRED EMBODIMENT

In order to make the above purposes, features, and advantages of the present invention more obvious and comprehensible, specific embodiments of the present invention are described in detail below. Many specific details are set forth in the following description in order to fully understand the present invention. However, the present invention can be implemented in many other ways than those described herein, and a person skilled in the art can make similar improvements without departing from the intension of the present invention, so the present invention is not limited by the specific implementations disclosed below.

The present embodiment provides a method for extracting a sweetening composition from leaves of *Rubus suavissimus* S. Lee, and the method comprises the following steps:

1) Pretreatment: the dried leaves of *Rubus suavissimus* S. Lee were crushed, and then the branches, petioles, veins were separated from mesophyll fragments in the raw materials, and the mesophyll fragments were collected.

When picking leaves of *Rubus suavissimus* S. Lee, partial branches and all petioles were also brought into the raw materials. However, the branches and petioles contain only a trace amount of Rubusoside, and contain a large amount of bitter and astringent components which will increase the difficulty in subsequent separation and purification and will affect the taste and properties of the finished product, and simple treatment of the raw materials can remove these components.

Preferably, the mesophyll fragments are separated by a cyclonic separation method.

Preferably, the water content in leaves of *Rubus suavissimus* S. Lee before crushing is controlled to be about 12% to 20%. If there is too little water in the leaves, the branches, petioles, veins and mesophylls are easily broken into powder when crushing, and it is difficult to separate the branches, petioles and veins from mesophylls by cyclonic separation. If there is too much water in the leaves, the mesophylls are not easy to be broken, the quantity of the collected mesophylls is small and the loss is large.

The raw materials used in the present invention are dried leaves of *Rubus suavissimus* S. Lee, a plant of the genus *Rubus* of Rosaceae.

Organic *Rubus suavissimus* S. Lee refers to a *Rubus suavissimus* S. Lee, during the planting and growing process of which, the organic production regulations are strictly followed, the use of any chemically synthesized pesticides, fertilizers, growth regulators and other chemical substances is prohibited, and the use of genetic engineering and products thereof is prohibited, while the laws of nature and ecological principles are followed, and the *Rubus suavissimus* S. Lee has been certified by an organic food certification agency and an organic food certificate is issued therefor.

Preferably, the raw materials used in the present invention are dried leaves from plants of *Rubus suavissimus* S. Lee growing for two or more years and being harvested on May to July and from plants grown from the lateral roots and harvested on September to November in the same year.

Preferably, the raw materials used in the present invention are dried leaves from plants of organic *Rubus suavissimus* S. Lee growing for two or more years and being harvested on May to July and from plants grown from the lateral roots and harvested on September to November in the same year.

The dried leaves from plants of *Rubus suavissimus* S. Lee growing for two or more years and being harvested on May to July and from plants grown from the lateral roots harvested on September to November in the same year, have a high content of Rubusoside, a high weight of leaves and a large yield. The local climate from May to July and from September to November is suitable for air-drying and sun-drying.

The above mesophyll fragments were allowed to contact with water for a sufficient time, and then solid-liquid separation was performed to obtain an extract solution containing a sweetening composition.

2) A continuous countercurrent extraction method was used.

It should be noted that the continuous countercurrent extraction means that the materials and the solvent move continuously at the same time, but the materials and the solvent move in the opposite direction during the extraction process. The materials enter from a head end and exits from a terminal end, and the solvent enters from the terminal end and exits from the head end. The extraction solvent is constantly renewed, so that a good mass transfer process between the materials and the solvent is always maintained. The main characteristics of the continuous countercurrent extraction include short extraction time and low solvent consumption.

Preferably, the duration of the continuous countercurrent extraction process is 30 to 120 min, and the ratio of the weight of mesophyll fragments of *Rubus suavissimus* S. Lee to the amount of purified water (material-to-liquid ratio w/w) during the extraction process is 1 kg:(3 to 6) L. The extraction temperature is controlled between 40 and 90° C. The solid-liquid separation is achieved by squeezing with a squeezer and filtering through a ceramic membrane.

Further preferably, in the above-mentioned continuous countercurrent method, two continuous countercurrent extractors were connected in series, and a squeeze juicer was connected in series behind each countercurrent extractor, so that mesophyll fragments were subjected to countercurrent extraction in the first countercurrent extractor, and then squeezed in the first squeeze juicer. The squeezed mesophyll fragments were dispersed, and subjected to countercurrent extraction in the second countercurrent extractor, and then squeezed in the second squeeze juicer to give mesophyll waste residues without sweet taste. In this method, the residues of mesophyll fragments after the first squeezing can allow water containing low-concentration sweet components to enter the residues more easily in the second countercurrent extraction, which can significantly shorten the extraction time. In some Examples, different numbers of continuous countercurrent extractors and squeeze juicers can be connected in series as needed. For example, three continuous countercurrent extractors and three squeeze juicers were connected in series, and one continuous countercurrent extractor and one squeeze juicer were connected in series.

In other preferred embodiments of the present invention, extraction was performed by a high-pressure jet extraction method.

High-pressure jet extraction refers to an extraction method which is performed by the following steps: conveying an extraction solvent after being pressurized to a high-pressure pipeline, allowing the solvent to pass through a nozzle, of which the pore diameter is much smaller than the inner diameter of the high-pressure pipeline, at a higher speed such that the water flow converges to form a high-pressure jet after passing through the nozzle, wherein high-pressure jets of different shapes can be formed by changing the shape of the nozzle; and then extracting using a solvent by a high-pressure jet manner. The high-pressure jet can play a role of crushing, mechanical stirring and cavitating the materials to be extracted, so as to improve the extraction efficiency and speed. The optimal extraction effect is achieved by adjusting the factors such as temperature, pressure, flow rate, and shape of the high-pressure jet, and the number and arrangement of the nozzles, extraction time, solvent type, material-to-liquid ratio, and the number of times of extraction.

Preferably, the extraction process of the high-pressure jet is performed for 15 to 180 min, the fluid temperature is 5 to 100° C., and the fluid pressure is 3 to 100 MPa. During the extraction process, the ratio of the weight of mesophyll fragments of *Rubus suavissimus* S. Lee to the amount of purified water (material-to-liquid ratio w/w) is (1:3) to (1:15), and the number of tunes of extraction is 1 to 3. The solid-liquid separation is achieved by centrifuging with a centrifuge and filtering through a ceramic membrane.

3) The phenolic hydroxyl-containing components in the above extract solution obtained were removed.

The leaves of *Rubus suavissimus* S. Lee contain a large quantity of phenolic hydroxyl-containing substances: sweet tea polyphenols (gallic acid, ellagic acid and the like) accounting for 6% to 18% by weight of dry leaves, and free flavones (kaempferol, quercetin, phloretin, luteolin and the like) and flavonoid glycosides, accounting for 1% to 6% by weight of dry leaves. Most of these components have an obvious bitter taste and colors. The higher the content of these components, the higher the absorbance under irradiation of light of 270 to 370 nm.

In this specific embodiment, a polar macroporous adsorption resin chromatography column was used to adsorb the phenolic hydroxyl-containing impurities in the extract solution, the chromatography column was washed with appropriate amount of water, and the effluent and water washing solution were collected. Further, the polar macroporous adsorption resin is selected from a styrene-divinylbenzene resin with a skeleton structure containing groups such as amide, sulfoxide and cyano, and a polyacrylic resin with a skeleton structure containing groups such as amide, sulfoxide and cyano, wherein the macroporous resin with strong polarity is selected from a styrene-divinylbenzene resin with a skeleton structure of phenolic resin or a skeleton structure containing groups such as amino, pyridine and nitrogen oxide, or a polyacrylic resin with a skeleton structure containing groups such as amino, pyridine and nitrogen oxide.

Wherein, the components with strong polarity will be adsorbed by the polar macroporous adsorption resin, and it is difficult for water to desorb these components. The monosaccharides, disaccharides, and partial amino acids in the extract solution are not easy to be adsorbed and easy to flow out with the solution. Rubusoside and the rest diterpene glycoside components such as Steviolmonoside, Suavioside A, and Suaviosides B, G, H, I and J and the like are not only adsorbed, but also desorbed by a water solution. Compared with diterpene glycoside components, phenolic hydroxyl-containing polyphenols and flavonoids are more easily adsorbed by a polar or strongly polar macroporous resin, and an alcohol solution with a high content is required in order to desorb these phenolic hydroxyl-containing components. The phenolic hydroxyl-containing components were removed according to the above principle.

In some preferred embodiments, a precipitating agent was used to remove a part of the phenolic hydroxyl-containing components before adsorbing the phenolic hydroxyl-containing components in the extract solution using a polar macroporous adsorption resin chromatography column. A precipitating agent corresponding to 3% to 15% by weight of the raw materials to be extracted was added into the extract solution to precipitate the phenolic hydroxyl-containing components. The solution temperature was kept above 60° C., stirred for 1 to 3 h, and cooled to normal temperature. The precipitate can be removed using any centrifugation and filtration method known in the art, the resulting liquid phase was collected, and the pH value thereof was adjusted until it was weakly acidic (3 to 6). Wherein, the precipitating agent is one or more of quicklime, slaked lime, and calcium bicarbonate. The precipitated impurities can be collected and dissolved with an appropriate acid solution, so as to be further processed into polyphenols of *Rubus suavissimus* S. Lee and flavones of *Rubus suavissimus* S. Lee. The phenolic hydroxyl-containing components adsorbed in the resin can be desorbed with a suitable solvent and used to produce polyphenols of *Rubus suavissimus* S. Lee and flavones of *Rubus suavissimus* S. Lee. With a precipitating agent such as quicklime, most phenolic hydroxyl-containing substances such as polyphenols and flavones, and partial protein components can be precipitated at a temperature of 50° C. to 60° C. The burden of subsequent resin treatment can be reduced, and the combination of the both can remove the phenolic hydroxyl-containing components with a more obvious effect.

4) The liquid with phenolic hydroxyl-containing components removed was concentrated and purified by a nanofiltration membrane.

In some preferred embodiments, the liquid with phenolic hydroxyl-containing components removed was concentrated and purified with a nanofiltration membrane having a pore size of 1 to 2 nm to obtain a retentate solution. The materials of the nanofiltration membrane are generally polyamide, cellulose acetate, polyvinyl alcohol, sulfonated polysulfone, sulfonated polyethersulfone, inorganics, metals and the like. Preferably, an inorganic nanofiltration membrane with a pore size of 1 to 2 nm was used for concentration and purification. The inorganic nanofiltration membrane may be a $SiO_2$ membrane, an $Al_2O_3$ membrane, a $TiO_2$ membrane, a $ZrO_2$ membrane, or a composite membrane thereof. Concentration and purification by nanofiltration can remove most of the water, inorganic salts, amino acids, monosaccharides, disaccharides and the like. After concentration and purification by nanofiltration, the nanofiltration membrane retentate solution still contains components such as inorganic salts, amino acids, monosaccharides, disaccharides. Generally, the concentrated solution needs to be diluted again with an appropriate amount of purified water, and then concentrated and purified by nanofiltration again, and the above steps were repeated for many times to remove the components such as inorganic salts, amino acids, monosaccharides, disaccharides, organic acids. Further preferably, purified water that is twice the volume of the concentrated solution was added each time, and a retentate solution was obtained by repeating for 1 to 4 times.

5) The retentate solution from nanofiltration was crystallized in water phase.

In some preferred embodiments, the retentate solution was frozen and crystallized in water phase under ultraviolet light irradiation, and then recrystallized. The retentate solution with a solid content of 20% to 40% (w/w) was frozen quickly below 0° C. into a solid, and then heated to 0° C. to 10° C. to thaw it, and Rubusoside precipitated to form an ice cream-like white fluid. Crystals (wet) and mother liquor can be obtained by any suitable methods of centrifugation and filtration known in the art. The entire process was performed under ultraviolet light irradiation. These crystals contain more than 40% of water, and can dissolve under heating, and purified water of 0 to 10 times the weight of crystals was added. When no water was added, the wet crystals can also form a solution state after being heated and recrystallization can also be performed. Then the above steps of freezing and crystallization were repeated to obtain recrystallized crystals (wet) and recrystallization mother liquor. The whole process was performed under ultraviolet light irradiation. Generally, the solid content (w/w) of the concentrated solution obtained by the nanofiltration membrane retention was only about 10% to 20%. Therefore, the concentrated solution can be made thicker by any suitable concentration method known in the art so that Rubusoside was frozen and crystallized in the water phase. The above mother liquor and recrystallization mother liquor were concentrated into concentrates having a solid content of 30% to 60% by a suitable concentration method. The concentrated solution of the crystallization mother liquor, the crystals, the concentrated solution of the recrystallization mother liquor, and the recrystallized crystals are all sweetening compositions of *Rubus suavissimus* S. Lee, and the water solution (with a solid content of 1%, w/w) of the sweetening composition has an absorbance of less than 0.4 at the wavelength of 270 to 370 nm. Ultraviolet light irradiation promotes the crystallization of Rubusoside. After crystallization, the total recovery rate of Rubusoside based on the crystals and the mother liquor was more than 100%, up to about 104% to 108%. It can be seen that the rest diterpene glycoside components in the leaves of *Rubus suavissimus* S. Lee were converted into Rubusoside under the condition of ultraviolet light irradiation, thereby improving the recovery rate of Rubusoside.

In some preferred embodiments, in order to meet the needs of the market, the concentrated solution of the above-mentioned crystallization mother liquor, crystals, the concentrated solution of the recrystallization mother liquor and the recrystallized crystals need to be further dried, so as to obtain a powdery or solid sweetening composition of *Rubus suavissimus* S. Lee. Based on the content of Rubusoside in the obtained powders, the sequence from low to high content is mother liquor powder (50% to 65%), recrystallization mother liquor powder (65% to 85%), crystal powder (85% to 95%), and recrystallized crystal powder (95% to 99% or more). The above powders are milky white to pure white powders, and the higher the content, the whiter the color. In the powdery sweetening composition, when the content of Rubusoside is 50% to 70%, the water solubility is good, and it is not easy to form crystal precipitates; while when the content of Rubusoside is 90% to 99%, it is very easy to precipitate in the form of crystals in a water solution. The absorbance of the water solution (with a solid content of 1%, w/w) of the above sweetening composition is less than 0.4 at the wavelength of 270 to 370 nm. The drying method can be spray drying, vacuum drying, freeze drying, fluidized dryer, circulating hot air drying and the like.

In some embodiments, without water phase crystallization under ultraviolet light irradiation, the retentate solution from nanofiltration may be directly further concentrated or further concentrated and dried to obtain a sweetening composition, which contains 70% to 85% Rubusoside based on dry weight, and the absorbance of the water solution (with a solid content of 1%, w/w) of the sweetening composition is less than 0.4 at the wavelength of 270 to 370 nm. Preferably, the retentate solution was concentrated so that the solid content (w/w) of the concentrated solution is 60% to 70%, or the sugar content is about 65 Brix. Preferably, the retentate solution was concentrated to a suitable concentration, and then dried to obtain a powdery sweetening composition of about 80 mesh.

The method of the present invention is suitable for large-scale production of a sweetening composition, and is also suitable for producing an organic sweetening composition from raw materials of the leaves of organic *Rubus suavissimus* S. Lee.

Different batches and different specifications of the sweetening compositions produced from the same raw materials (the common *Rubus suavissimus* S. Lee was distinguished from the organic *Rubus suavissimus* S. Lee) can be mixed, so as to meet the market requirements for specific contents (such as 70% Rubusoside, 85% Rubusoside, 90% Rubusoside, 95% Rubusoside, all of which are calculated according to the dry weight).

The specific embodiment further includes a sweetening composition obtained by using the above method for extracting the sweetening composition from the leaves of *Rubus suavissimus* S. Lee.

The present Example also includes the use of the above sweetening composition in the preparation of a composite sweetener. This composite sweetener may be the following composition A, or a mixture of the composition A and the composition B.

Composition A: a sweetening composition of *Rubus suavissimus* S. Lee obtained from the raw materials of *Rubus suavissimus* S. Lee by the method described in "A method for preparing a sweetening composition from the leaves of *Rubus suavissimus* S. Lee" above. The main components of the sweetening composition of *Rubus suavissimus* S. Lee comprise 50% to 99% of Rubusoside; other sweet diterpene glycosides in *Rubus suavissimus* S. Lee: Steviolmonoside, Suavioside A and Suaviosides B, G, H, I and J; and the rest components extracted from *Rubus suavissimus* S. Lee. The absorbance of the water solution (with a solid content of 1%, w/w) of the sweetening composition is less than 0.4 at the wavelength of 270 to 370 nm.

Composition B: one or more ingredients, which may be one or more of sweeteners, essences, spices, flavoring agents, pigments, plant extracts, and excipients.

Preferably, the raw material used to produce composition A is organic *Rubus suavissimus* S. Lee.

In some preferred embodiments, the composite sweetener is Composition A, which is white crystal or fluid ice cream-like white crystal, contains 90% to 99% of Rubusoside based on dry weight, and has an absorbance of less than 0.4 at the wavelength of 270 to 370 nm after being dissolved into an aqueous solution (with a solid content of 1%, w/w).

In some preferred embodiments, the composite sweetener is Composition A, which is a solid or a powder, contains 50% to 99% of Rubusoside based on dry weight, and has an absorbance less than 0.4 at the wavelength of 270 to 370 nm after being dissolved into an aqueous solution (with a solid content of 1%, w/w).

A person skilled in the art can add the above-mentioned composite sweeteners into foods, beverages, health products, daily chemicals or medicines according to need.

That is, the third purpose of the present invention is to provide foods, beverages, health products, daily chemicals, medicines, and the like containing the sweetening composition described above.

The present invention can remove the bitter and astringent components of *Rubus suavissimus* S. Lee, which are difficult to be removed in subsequent processes, by a simple pretreatment method for the raw materials of *Rubus suavissimus* S. Lee. The method of continuous countercurrent extraction combined with squeezing extraction improves the extraction rate and meanwhile shortens the extraction time. Alternatively, a high-pressure jet extraction method was applied to the production process of the sweetening composition of *Rubus suavissimus* S. Lee. This extraction method can play a role of cavitating, mechanical stirring, and crushing, and has high extraction efficiency. A polar macroporous adsorption resin was used to remove the phenolic hydroxyl-containing components, with no need for a conventional complex process comprising adsorbing sweet components, then desorbing with an alcohol solution, and decolorizing. The process is simple, and the phenolic hydroxyl-containing components with deep color can be effectively removed by combining with concentration and purification by nanofiltration. The crystallization in the water phase under ultraviolet light irradiation can play a role of promoting crystallization, the recovery rate is high, and sweetening compositions of a plurality of specifications and colors ranging from white like to pure white can be simultaneously produced. The whole process endows the sweetening composition with pure sweetness, white color, and light bitter and astringent taste. Moreover, in the preparation process of the sweetening composition of the present invention, only purified water is used and no organic solvents such as ethanol are used, and thus the production process is green and healthy, and is also suitable for the production of organic products of *Rubus suavissimus* S. Lee.

In order to further illustrate the method for preparing a sweetening composition from the leaves of *Rubus suavissimus* S. Lee in the specific embodiment, some Examples are listed below in detail:

EXAMPLE 1

The present Example provides a method for preparing a sweetening composition from the leaves of *Rubus suavissimus* S. Lee, specifically comprising the following steps:

1) Pretreatment: 20 kg (with a Rubusoside content of 5.2%) of dry leaves of organic *Rubus suavissimus* S. Lee growing for two or more years and being harvested on October were taken, the water content of the dry leaves was controlled to about 15%, then the dry leaves were crushed and subjected to cyclonic separation by adjusting the inlet air speed, and the mesophyll fragments were collected and delivered to the extraction procedure.

2) Extraction: the mesophyll fragments were poured into a high-pressure jet extraction kettle, the extraction solvent was purified water, the extraction temperature was 40° C., the fluid pressure was 50 MPa, the ratio of material to liquid was 1:15, the extraction time was 30 min, and the extraction was performed once, and then centrifugation was performed by a horizontal screw centrifuge, and filtration was performed by a ceramic membrane to obtain an extract solution.

3) Removal of phenolic hydroxyl-containing components: the extract solution was loaded on 40 L of macroporous adsorption resin XAD761 available from Sunresin New Materials Co., Ltd. having a phenolic-type skeleton structure, the flow rate was 2 BV/h, 1 BV of purified water was used for washing at the same flow rate, the effluent and water washing solution were collected, and purified with a nanofiltration membrane.

4) Concentration and purification by a nanofiltration membrane: a $SiO_2$ membrane with a pore size of 2 nm was used for nanofiltering concentration and purification. Concentration was performed till the retentate solution was about 3 L, 6 L of purified water was added for diluting, nanofiltrering concentration was continued till about 3 L, and the process of diluting and then concentrating was repeated for 3 times to obtain 3 L of a slightly yellow transparent retentate solution. The retentate solution was concentrated under reduced pressure to a solid content of 40% (w/w) and delivered to the crystallization procedure. 5) Crystallization in water phase under ultraviolet light irradiation: the nanofiltration membrane retentate solution was rapidly frozen into a solid in a freezer under ultraviolet light irradiation, and then thawed, then the retentate solution was subjected to crystallization for 10 h while the temperature was held at about 2° C., to obtain an ice cream-like white fluid, the resultant was subjected to vacuum filtration to obtain crystals, purified water in an amount of 5 times the weight of the crystals was added to the crystals, the above crystallization step was repeated and lasted for 5 h, and vacuum filtration was performed to obtain recrystallized crystals. The recrystallized crystals were vacuum dried and pulverized to give 0.67 kg of pure white powdery sweetening composition I having a specification of 95% to 99% of Rubusoside. The crystallization mother liquor was concentrated to 65 Brix under reduced pressure to obtain 0.78 kg of a light yellow extract-like sweetening composition II, which has a specification of 50% to 65% of Rubusoside based on dry weight. The recrystallization mother liquor was concentrated under reduced pressure, dried under vacuum, and pulverized to obtain 0.11 kg of a sweetening composition III having a specification of 65% to 85% of Rubusoside.

EXAMPLE 2

The present Example provides a method for preparing a sweetening composition from the leaves of *Rubus suavissimus* S. Lee, specifically comprising the following steps:

1) Pretreatment: 2000 kg (with a Rubusoside content of 4.34%) of dry leaves of organic *Rubus suavissimus* S. Lee growing for two or more years and being harvested on October were taken, the water content of the dry leaves was controlled to about 15%, then the dry leaves were crushed and subjected to cyclonic separation by adjusting the inlet air speed, and the mesophyll fragments were collected and delivered to the extraction procedure.

2) Extraction: the mesophyll fragments were fed to two sets of continuous countercurrent extractors connected in series, the mesophyll fragments were sequentially passed through a continuous countercurrent extractor A, a squeezer A, a continuous countercurrent extractor B, and a squeezer B, the extraction time when the mesophyll fragments contact with purified water was 40 min, the purified water used in the extraction process was 8000 L, the extraction temperature was 40° C., and an extract solution was obtained by squeezing with a squeezer.

3) Removal of phenolic hydroxyl-containing components: 400 kg of slaked lime was added to the extract solution, stirred for 1 h at 60° C., and cooled to room temperature, the resultant was centrifuged with a horizontal screw centrifuge, the residues from centrifugation was washed with a small amount of purified water, and dehydrated with a multi-disc screw dehydrator, the centrifugate and the dehydrating solution were collected, and the pH value was adjusted until it is weakly acidic (3 to 6), the centrifugate and the dehydrating solution were loaded on 1000 L of styrene-divinylbenzene macroporous adsorption resin HPD-600 available from Beijing Solarbio Science & Tecnology Co., Ltd. with a skeleton structure containing groups such as cyano, with a flow rate of 2 BV/h, washing was performed with 1 BV of purified water at the same flow rate, the effluent and water washing solution were collected and purified with a nanofiltration membrane.

4) Concentration and purification by a nanofiltration membrane: a $TiO_2$—$ZrO_2$ composite membrane with a pore size of 1 nm was used for nanofiltrering concentration and purification. Concentration was performed till the retentate solution was about 250 L, 500 L of purified water was added for diluting, nanofiltering concentration was continued till about 250 L, and the process of diluting and then concentrating was repeated for 2 times to obtain 250 L of a slightly yellow transparent retentate solution. The retentate solution was concentrated under reduced pressure to a solid content of 30% (w/w) and delivered to the crystallization procedure.

5) Crystallization in water phase under ultraviolet light irradiation: the nanofiltration membrane retentate solution was rapidly frozen into a solid in a freezer under ultraviolet light irradiation, and then thawed, then the retentate solution was subjected to crystallization for 15 h while the temperature was held at 5° C., to obtain an ice cream-like white fluid, the resultant was centrifuged with a plate centrifuge to obtain crystals, the crystals were heated to a liquid state, and then spray-dried to obtain 70.13 kg of a white powdery sweetening composition IV having a specification of 85% to 95% of Rubusoside. The crystallization mother liquor was concentrated to a suitable concentration under reduced pressure, and then spray-dried to obtain 33.43 kg of a white-like sweetening composition V having a specification of 50% to 65% of Rubusoside.

EXAMPLE 3

The present Example provides a method for preparing a sweetening composition from the leaves of *Rubus suavissimus* S. Lee, specifically comprising the following steps:

1) Pretreatment: 2000 kg (with a Rubusoside content of 4.95%) of dry leaves of *Rubus suavissimus* S. Lee growing for two or more years and being harvested on November were taken, the water content of the dry leaves was controlled to about 12%, then the dry leaves were crushed and subjected to cyclonic separation by adjusting the inlet air speed, and the mesophyll fragments were collected and delivered to the extraction procedure.

2) Extraction: the mesophyll fragments were fed to a continuous countercurrent extractor unit, the extraction time of the mesophyll fragments in contact with purified water was 90 min, the purified water used in the extraction process was 12000 L, the extraction temperature was 60° C., and an extract solution was obtained by squeezing with a squeezer and filtering by a ceramic membrane.

3) Removal of phenolic hydroxyl-containing components: the extract solution was loaded on 2000 L of polyacrylic-type macroporous adsorption resin LX-17 available from Sunresin New Materials Co. Ltd. with a skeleton structure containing groups such as nitrogen oxide, the flow rate was 2 BV/h, 3 BV of purified water was used for washing at the same flow rate, and the effluent and water washing solution were collected and purified with a nanofiltration membrane.

4) Concentration and purification by a nanofiltration membrane: a $TiO_2$—$ZrO_2$ composite membrane with a pore size of 1 nm was used for nanofiltering concentration and purification. Concentration was performed till the retentate solution was about 400 L, 800 L of purified water was added for diluting, nanofiltering concentration was continued till about 400 L, and the process of diluting and then concentrating was repeated for 4 times to obtain 400 L of a slightly yellow transparent retentate solution. The retentate solution was spray-dried to obtain 121.98 kg of a white powdery sweetening composition VI having a specification of 70% to 85% of Rubusoside.

Comparative Example 1

1) Pre-treatment: dry leaves of *Rubus suavissimus* S. Lee growing for two or more years and being harvested on November were taken, the water content of the dry leaves was controlled to about 12%, then the dry leaves were crushed and subjected to cyclonic separation by adjusting the inlet air speed, and after the mesophyll fragments were collected, 20 kg of petiole and leaf stalk tissues were selected and delivered to the extraction procedure.

2) Extraction: 20 kg of the above-mentioned petiole and leaf stalk tissues were poured into a high-pressure jet extraction kettle, the extraction solvent was purified water, the extraction temperature was 40° C., the fluid pressure was 50 MPa, the material-to-liquid ratio was 1:15, the extraction time was 30 min, and the extraction was performed once, and then centrifugation was performed by a horizontal screw centrifuge, and filtration was performed by a ceramic membrane to obtain an extract solution.

3) Removal of phenolic hydroxyl-containing components: the extract solution was loaded on 40 L of macroporous adsorption resin XAD761 having a phenolic-type skeleton structure, the flow rate was 2 BV/h, 1 BV of purified water was used for washing at the same flow rate, and the effluent and water washing solution were collected, and purified with a nanofiltration membrane.

4) Concentration and purification by a nanofiltration membrane: a $SiO_2$ membrane with a pore size of 2 nm was used for nanofiltering concentration and purification. Concentration was performed till the retentate solution was about 3 L, 6 L of purified water was added for diluting, nanofiltering concentration was continued till about 3 L, and the process of diluting and then concentrating was repeated for 3 times to obtain 3 L of a slightly yellow transparent retentate solution. The retentate solution was concentrated under reduced pressure to a solid content of 40% (w/w), and dried under vacuum to obtain 0.11 kg of a bitter powder VII.

The sweetening compositions I, II, III, IV, V and VI obtained in Examples 1, 2, and 3, and the bitter powder VII were detected by the following HPLC method for the content of Rubusoside:

The Rubusoside content was measured with acetonitrile-sodium phosphate buffer solution (1.2 g of sodium dihydrogen phosphate was dissolved in 800 ml of water, the pH was adjusted to 2.6 with phosphoric acid) at a ratio of 32:68 as a mobile phase, a detection wavelength of 210 nm, a column temperature of 40° C., a flow rate of 1 ml/min, a sample volume of 10 ul, and a chromatographic column of C18 column (4.6 mm*150 mm, 5 μm).

A water solution with a solid content of 1% (w/w) was prepared from the sweetening compositions I, II, III, IV, V and VI, and the bitter powder VII, obtained in Examples 1, 2, 3, and Comparative Example 1, respectively using purified water, and subjected to ultraviolet light irradiation at a wavelength of 270 to 370 nm, and the results of the maximum absorption value measured were shown in Table 1. It can be known from Table 1 that the maximum absorbance of the six sweetening compositions at the wavelength of 270 to 370 nm are all less than 0.4, indicating that the content of the phenolic hydroxyl-containing components is low, the phenolic hydroxyl-containing components are well removed, and the maximum Rubusoside content in the sweetening compositions can reach up to 98.14%.

Figure 1:
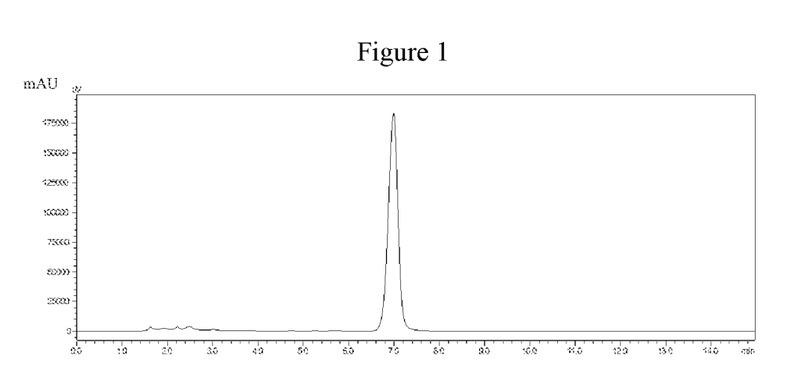
FIG. 1 is an HPLC chromatogram of the sweetening composition I obtained in Example 1 of the present invention.
Figure 2:
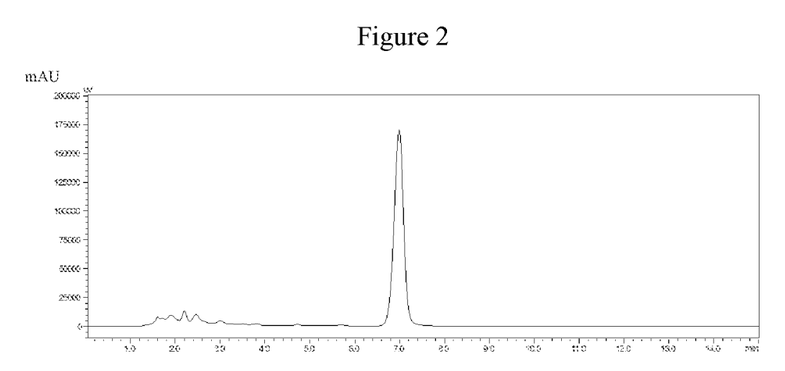
FIG. 2 is an HPLC chromatogram of the sweetening composition III obtained in Example 1 of the present invention.
Figure 3:
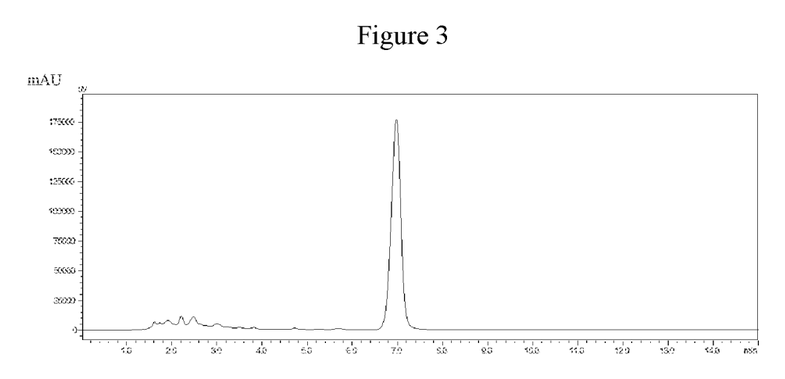
FIG. 3 is an HPLC chromatogram of the sweetening composition IV obtained in Example 2 of the present invention.
Figure 4:
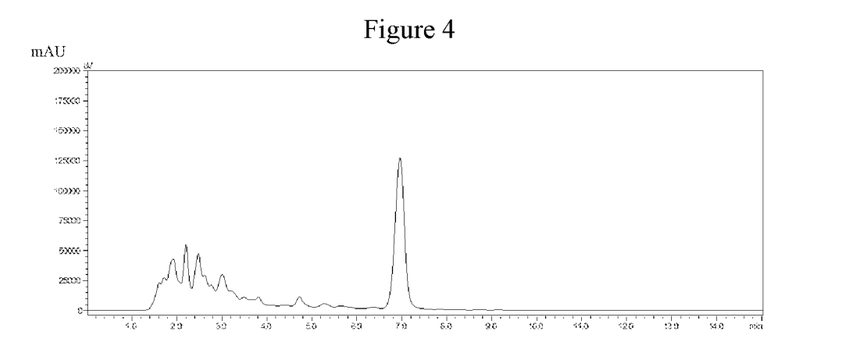
FIG. 4 is an HPLC chromatogram of the sweetening composition V obtained in Example 2 of the present invention.
Figure 5:
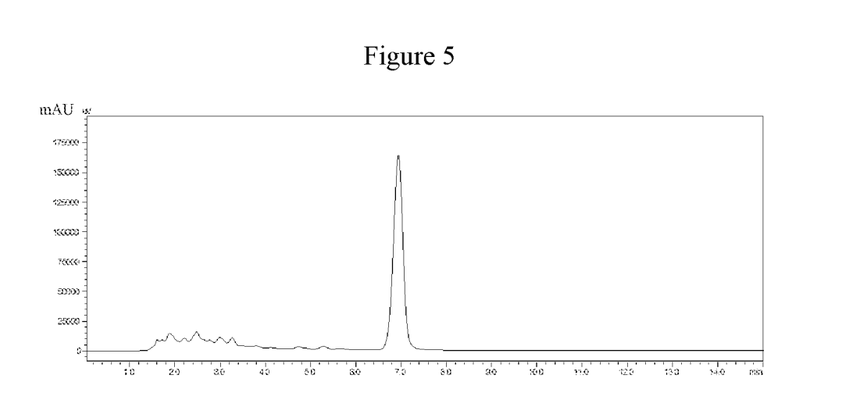
FIG. 5 is an HPLC chromatogram of the sweetening composition VI obtained in Example 3 of the present invention.
Figure 6:
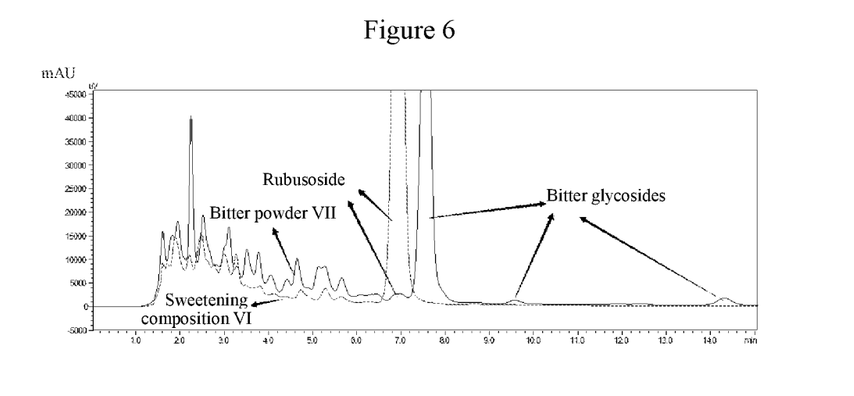
FIG. 6 is a comparison of the HPLC chromatograms of the sweetening composition F obtained in Example 3 of the present invention and the bitter powder G obtained in Comparative Example 1.

In combination with FIGS. 1 to 5, the main components of each composition are also fully explained. In combination with FIG. 6, we can see that the peak of Rubusoside in the chromatogram of Comparative Example 1, which uses the petioles and leaf stalks of *Rubus suavissimus* S. Lee as raw materials, is very small, and the peak of the bitter glycosides is very high. Therefore, the bitter glycosides that are difficult to separate in subsequent processes can be effectively removed by simple pretreatment of the raw materials.

TABLE 1

Table of results of Rubusoside content and absorbance of the sweetening compositions obtained in Examples 1 to 3

| Compositions | Rubusoside (% w/w) | Maximum absorbance at 270 to 370 nm (AU) |
| --- | --- | --- |
| Sweetening composition I | 98.14 | 0.13 |
| Sweetening composition II | 59.14 | 0.35 |
| Sweetening composition III | 83.11 | 0.22 |
| Sweetening composition IV | 93.84 | 0.15 |
| Sweetening composition V | 62.78 | 0.33 |
| Sweetening composition VI | 79.54 | 0.28 |
| Bitter powder VII | 0.51 | 0.31 |

Unless defined otherwise, all technical and scientific terms used herein have the same meaning as commonly understood by a person skilled in the art to which the present invention belongs. The terms used herein in the description of the present invention is for the purpose of describing specific examples only and is not intended to limit the present invention. The technical features of the examples described above can be arbitrarily combined. In order to simplify the description, all possible combinations of the technical features in the above examples have not been described. However, as long as there is no contradiction in the combinations of these technical features, the combinations should be considered within the scope described in the description.

INDUSTRIAL APPLICABILITY

The present invention provides a sweetening composition and a preparation method and use thereof. The method comprises the steps of obtaining mesophyll fragments of *Rubus suavissimus* S. Lee, extracting with water as a solvent, removing phenolic hydroxyl-containing components, concentrating, purifying, and water-phase crystallization to obtain a sweetening composition. The present invention also includes the sweetening composition obtained by this method and the use of the sweetening composition in foods, beverages, health products, daily chemicals and medicines. The sweetening composition prepared by the preparation method of the present invention is white in color, with unobvious bitter and astringent taste. The sweetening composition contains 50% to 99% of Rubusoside based on a dry weight, and has an absorbance of less than 0.4 at the wavelength of 270 to 370 nm after being dissolved and prepared into an aqueous solution (with a solid content of 1%, w/w). By removing bitter glycosides and phenolic hydroxyl-containing components, the present invention makes the flavor of the sweetening composition better. In the preparation process of the sweetening composition of the present invention, only purified water is used and no organic solvents such as ethanol are used, and thus the production process is green and healthy, and is also suitable for the production of organic products of *Rubus suavissimus* S. Lee. The preparation method of the present invention has good economic value and application prospects.

What is claimed is:

1. A method for preparing a sweetening composition from the leaves of *Rubus suavissimus* S. Lee, comprising:
    S1. pretreatment: crushing raw materials, removing a solid of a leaf tissue including glycoside from a solid of the raw materials by a cyclonic separation, separating mesophyll fragments from the raw materials, and collecting the mesophyll fragments;
    S2. extraction: extracting the mesophyll fragments with water as a solvent to obtain an extract solution;
    S3. removal of phenolic hydroxyl-containing components: allowing the extract solution to pass through a polar macroporous adsorption resin such that the phenolic hydroxyl-containing components are adsorbed, and collecting an effluent;
    S4. concentration and purification with a nanofiltration membrane: allowing the effluent collected in said S3 to pass through a nanofiltration membrane with a pore diameter of 1 to 2 nm for concentrating and purifying, and retaining a retentate solution; and
    S5. water-phase crystallization: freezing the retentate solution obtained in said S4 into a solid, then thawing, and crystallizing at a temperature of 0° C. to 10° C. to obtain crystals of a sweetening composition.

2. The method for preparing a sweetening composition from the leaves of *Rubus suavissimus* S. Lee according to claim 1, wherein, in said S2, said extracting of the mesophyll fragments is performed with water as a solvent using a continuous countercurrent extractor to obtain an extract mixture, and then the extract mixture is squeezed with a squeezer, followed by filtering to obtain the extract solution.

3. The method for preparing a sweetening composition from the leaves of *Rubus suavissimus* S. Lee according to claim 2, wherein the extraction time for obtaining the extract mixture by extracting using a continuous countercurrent extractor is 30 to 120 min, the extraction temperature is 40 to 90° C., and the material-to-liquid ratio of the crushed leaves of *Rubus suavissimus* S. Lee to the water is 1 kg: (3 to 6) L.

4. The method for preparing a sweetening composition from the leaves of *Rubus suavissimus* S. Lee according to claim 1, wherein, in said S2, said extracting of the mesophyll fragments is performed with water as a solvent using a high-pressure jet extractor, followed by centrifuging and filtering to obtain the extract solution.

5. The method for preparing a sweetening composition from the leaves of *Rubus suavissimus* S. Lee according to claim 4, wherein, the time for performing the extraction using a high-pressure jet extractor is 15 to 180 min, fluid temperature is 5 to 100° C., fluid pressure is 3 to 100 MPa, and the material-to-liquid ratio of the crushed leaves of *Rubus suavissimus* S. Lee to the water is 1 kg: (3 to 5) L.

6. The method for preparing a sweetening composition from the leaves of *Rubus suavissimus* S. Lee according to claim 1, wherein, prior to said S3, the method further comprises adding a precipitating agent to the extract solution and stirring, filtering, collecting a filtrate, and adjusting pH value of the filtrate to 3 to 6.

7. The method for preparing a sweetening composition from the leaves of *Rubus suavissimus* S. Lee according to claim 6, wherein the precipitating agent is added to the extract solution at a temperature of 50 to 60° C., and the precipitating agent is one or more of quicklime, slaked lime and calcium bicarbonate.

8. The method for preparing a sweetening composition from the leaves of *Rubus suavissimus* S. Lee according to claim 1, wherein, in said S5, the retentate solution is subjected to the freezing, thawing and crystallizing, under ultraviolet light irradiation,
and/or, in said S3, the polar macroporous adsorption resin is selected from a phenolic resin, or a styrene-divinylbenzene resin containing one or more of amide, sulfoxide, cyano, amino, pyridine, and nitrogen oxide groups, or a polyacrylic resin containing one or more of amide, sulfoxide, cyano, amino, pyridine, and nitrogen oxide groups.

9. The method for preparing a sweetening composition from the leaves of *Rubus suavissimus* S. Lee according to claim 2, wherein, prior to said S3, the method further comprises adding a precipitating agent to the extract solution and stirring, filtering, collecting the filtrate, and adjusting the pH value of the filtrate to 3 to 6.

10. The method for preparing a sweetening composition from the leaves of *Rubus suavissimus* S. Lee according to claim 3, wherein, prior to said S3, the method further comprises adding a precipitating agent to the extract solution and stirring, filtering, collecting the filtrate, and adjusting the pH value of the filtrate to 3 to 6.

11. The method for preparing a sweetening composition from the leaves of *Rubus suavissimus* S. Lee according to claim 4, wherein, prior to said S3, the method further comprises adding a precipitating agent to the extract solution and stirring, filtering, collecting the filtrate, and adjusting the pH value of the filtrate to 3 to 6.

12. The method for preparing a sweetening composition from the leaves of *Rubus suavissimus* S. Lee according to claim 5, wherein, prior to said S3, the method further comprises adding a precipitating agent to the extract solution and stirring, filtering, collecting the filtrate, and adjusting the pH value of the filtrate to 3 to 6.

13. The method for preparing a sweetening composition from the leaves of *Rubus suavissimus* S. Lee according to claim 2, wherein, in said S5, the retentate solution is subjected to the freezing, thawing and crystallizing, under ultraviolet light irradiation,
and/or, in said S3, the polar macroporous adsorption resin is selected from a phenolic resin, or a styrene-divinylbenzene resin containing one or more of amide, sulfoxide, cyano, amino, pyridine, and nitrogen oxide groups, or a polyacrylic resin containing one or more of amide, sulfoxide, cyano, amino, pyridine, and nitrogen oxide groups.

14. The method for preparing a sweetening composition from the leaves of *Rubus suavissimus* S. Lee according to claim 3, wherein, in said S5, the retentate solution is subjected to the freezing, thawing and crystallizing, under ultraviolet light irradiation,
and/or, in said S3, the polar macroporous adsorption resin is selected from a phenolic resin, or a styrene-divinylbenzene resin containing one or more of amide, sulfoxide, cyano, amino, pyridine, and nitrogen oxide groups, or a polyacrylic resin containing one or more of amide, sulfoxide, cyano, amino, pyridine, and nitrogen oxide groups.

15. The method for preparing a sweetening composition from the leaves of *Rubus suavissimus* S. Lee according to claim 4, wherein, in said S5, the retentate solution is subjected to the freezing, thawing and crystallizing, under ultraviolet light irradiation,
and/or, in said S3, the polar macroporous adsorption resin is selected from a phenolic resin, or a styrene-divinylbenzene resin containing one or more of amide, sulfoxide, cyano, amino, pyridine, and nitrogen oxide groups, or a polyacrylic resin containing one or more of amide, sulfoxide, cyano, amino, pyridine, and nitrogen oxide groups.

16. The method for preparing a sweetening composition from the leaves of *Rubus suavissimus* S. Lee according to claim 5, wherein, in said S5, the retentate solution is subjected to the freezing, thawing and crystallizing, under ultraviolet light irradiation,
and/or, in said S3, the polar macroporous adsorption resin is selected from a phenolic resin, or a styrene-divinylbenzene resin containing one or more of amide, sulfoxide, cyano, amino, pyridine, and nitrogen oxide groups, or a polyacrylic resin containing one or more of amide, sulfoxide, cyano, amino, pyridine, and nitrogen oxide groups.

17. The method according to claim 1, wherein petiole or leaf stalk are removed from the raw materials before collecting the mesophyll fragments during said S1 pretreatment.

18. The method according to claim 1, wherein the amount of water contained in the leaves of *Rubus suavissimus* S. Lee before crushing the raw materials is controlled to be about 12% to 20% in said S1 pretreatment.

* * * * *